(12) United States Patent
Morimoto et al.

(10) Patent No.: US 12,279,939 B2
(45) Date of Patent: *Apr. 22, 2025

(54) WEARABLE ARTICLE HAVING ELASTIC BELT

(71) Applicant: The Procter & Gamble Company, Cincinnati, OH (US)

(72) Inventors: Koichi Morimoto, Beijing (CN); Ling Tong, Beijing (CN); Chunmin Cheng, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 83 days.

This patent is subject to a terminal disclaimer.

(21) Appl. No.: 18/189,287

(22) Filed: Mar. 24, 2023

(65) Prior Publication Data
US 2023/0225914 A1 Jul. 20, 2023

Related U.S. Application Data

(63) Continuation of application No. 16/812,738, filed on Mar. 9, 2020, now Pat. No. 11,642,254, which is a
(Continued)

(51) Int. Cl.
*A61F 13/49* (2006.01)
*A61F 13/496* (2006.01)

(52) U.S. Cl.
CPC .. *A61F 13/49012* (2013.01); *A61F 13/49011* (2013.01); *A61F 13/49061* (2013.01);
(Continued)

(58) Field of Classification Search
CPC ...... A61F 13/49011; A61F 2013/49025; A61F 13/49012; A61F 13/49061; A61F 13/496;
(Continued)

(56) References Cited

U.S. PATENT DOCUMENTS

| 2,462,195 A | 2/1949 | Jacobson |
| 2,513,039 A | 6/1950 | Miller |

(Continued)

FOREIGN PATENT DOCUMENTS

| CN | 2167695 Y | 6/1994 |
| CN | 1246324 C | 3/2006 |

(Continued)

OTHER PUBLICATIONS

PCT Search Report and Written Opinion for PCT/CN2014/085248, dated May 26, 2015, 8 pages.
(Continued)

*Primary Examiner* — Susan S Su
(74) *Attorney, Agent, or Firm* — Charles R. Matson (57) ABSTRACT

A wearable article wherein least some of the elastic bodies may be arranged in at least 2 sets of a concentrated array defined as meeting: a) one concentrated array is formed by 2-4 elastic bodies; b) each elastic body within one concentrated array is disposed in an inner-interval between each elastic body of 2-4 mm; and c) one specific concentrated array disposed in an extra-interval between at least one neighboring elastic body outside the specific concentrated array of less than 8 mm. The entirety of the length of the belt side edge of the front belt may be seamed with a certain length of the belt side edge of the back belt to define a seam length LS. The front and back belts may each divided into 4 zones wherein at least 2 concentrated arrays are disposed on the front proximal tummy zone or the back distal tummy zone.

18 Claims, 9 Drawing Sheets

Related U.S. Application Data continuation of application No. 15/443,045, filed on Feb. 27, 2017, now Pat. No. 10,632,025, which is a continuation of application No. PCT/CN2014/091624, filed on Nov. 19, 2014, and a continuation-in-part of application No. PCT/CN2014/085248, filed on Aug. 27, 2014.

(52) U.S. Cl.
CPC ........ *A61F 13/496* (2013.01); *A61F 13/4963* (2013.01); *A61F 2013/49092* (2013.01)

(58) Field of Classification Search
CPC ........ A61F 13/4963; A61F 2013/49092; A61F 2013/49026
See application file for complete search history.

(56) References Cited

U.S. PATENT DOCUMENTS

| | | |
|---|---|---|
| 2,632,177 A | 3/1953 | Bigger |
| 3,080,869 A | 3/1963 | Alberts |
| 3,824,812 A | 7/1974 | Matthews et al. |
| D281,540 S | 12/1985 | Ternstrom |
| 5,787,512 A | 8/1998 | Knox |
| 5,876,392 A | 3/1999 | Hisada |
| 8,518,008 B2 | 8/2013 | Yoshioka et al. |
| 8,555,419 B2 | 10/2013 | Harvey et al. |
| 9,023,006 B2 | 5/2015 | Takino et al. |
| 9,358,162 B2 | 6/2016 | Kuwano et al. |
| 9,827,149 B2 | 11/2017 | Lavon |
| 10,064,763 B2 | 9/2018 | Takahashi et al. |
| 10,568,782 B2 | 2/2020 | Morimoto et al. |
| 10,632,024 B2 | 4/2020 | Morimoto et al. |
| 10,632,025 B2 | 4/2020 | Morimoto et al. |
| 2005/0107763 A1 | 5/2005 | Matsuda |
| 2005/0107764 A1 | 5/2005 | Matsuda |
| 2006/0036227 A1 | 2/2006 | Hoshino et al. |
| 2007/0208317 A1 | 9/2007 | Krautkramer et al. |
| 2008/0161768 A1 | 7/2008 | Baba |
| 2011/0106039 A1* | 5/2011 | Saito ................ A61F 13/49011 604/385.3 |
| 2011/0251576 A1 | 10/2011 | Ando et al. |
| 2012/0071852 A1 | 3/2012 | Tsang et al. |
| 2013/0060219 A1 | 3/2013 | Mukai et al. |
| 2013/0079742 A1 | 3/2013 | Kuwano et al. |
| 2013/0110075 A1 | 5/2013 | Mukai et al. |
| 2013/0123736 A1 | 5/2013 | Ichikawa |
| 2013/0211363 A1 | 8/2013 | Lavon |
| 2013/0226127 A1 | 8/2013 | Takahashi |
| 2013/0331807 A1 | 12/2013 | Ichihara et al. |
| 2014/0358110 A1 | 12/2014 | Takahashi et al. |
| 2016/0184145 A1 | 6/2016 | Morimoto |
| 2017/0143560 A1 | 5/2017 | Morimoto et al. |
| 2020/0206042 A1 | 7/2020 | Morimoto et al. |

FOREIGN PATENT DOCUMENTS

| | | |
|---|---|---|
| CN | 101389236 A | 3/2009 |
| EP | 2659870 A1 | 11/2013 |
| JP | H0871107 A | 3/1996 |
| JP | H0938134 A | 2/1997 |
| JP | H0966071 A | 3/1997 |
| JP | H9271488 A1 | 10/1997 |
| JP | 2000093461 A | 4/2000 |
| JP | 2001212176 A | 8/2001 |
| JP | 2007029479 A | 2/2007 |
| JP | 2007098161 A | 4/2007 |
| JP | 2007195647 A | 8/2007 |
| JP | 2009125087 A | 6/2009 |
| JP | 2012095937 A1 | 5/2012 |
| JP | 2012135519 A | 7/2012 |
| JP | 5566550 B1 | 6/2014 |
| JP | 2014150909 A5 | 8/2014 |
| WO | 2009031393 A1 | 3/2009 |
| WO | 2010082651 A1 | 7/2010 |
| WO | 2012029295 A1 | 3/2012 |
| WO | 2013046703 A1 | 4/2013 |
| WO | 2016029377 A1 | 3/2016 |
| WO | 2016029655 A1 | 3/2016 |

OTHER PUBLICATIONS

PCT Search Report and Written Opinion for PCT/CN2014/091624, dated Mar. 30, 2015, pp. 8.

PCT Supplementary Search Report and Written Opinion for CN2014/091624 dated Jun. 13, 2016, pp. 8.

All Office Actions: U.S. Appl. No. 15/443,045, filed on Feb. 27, 2017.

All Office Actions: U.S. Appl. No. 16/812,738, filed on Mar. 9, 2020.

* cited by examiner

WEARABLE ARTICLE HAVING ELASTIC BELT

CROSS REFERENCE TO RELATED APPLICATIONS

This application is a continuation of U.S. application Ser. No. 16/812,738, filed on Mar. 9, 2020, which is a continuation of U.S. application Ser. No. 15/443,045, filed on Feb. 27, 2017, which is a continuation of PCT Application No. PCT/CN2014/091624, filed on Feb. 4, 2015, and which is a continuation-in-part of PCT Application No. PCT/CN2014/085248, filed on Aug. 27, 2014; each of which are herein incorporated by reference in their entireties.

U.S. application Ser. No. 15/443,045 also claims foreign priority to Japanese Patent Application No. JP2014-237980, filed on Nov. 25, 2014 and claims foreign priority to Chinese Patent Application No. CN201510051309.8, filed on Jan. 30, 2015, each of which are herein incorporated by reference in their entirety.

FIELD OF THE INVENTION

The present invention relates to wearable articles having an elastic belt having arrays of elastic bodies.

BACKGROUND OF THE INVENTION

Infants and other incontinent individuals wear wearable articles such as diapers to receive and contain urine and other body exudates. Pull-on wearable articles, or pant-type wearable articles, are those which are donned by inserting the wearer's legs into the leg openings and sliding the article up into position about the lower torso. Pant-type absorbent articles have become popular for use on children who are able to walk and often who are toilet training, as well as for younger children who become more active in movement such that application of taped-type absorbent articles tend to be more difficult.

Many pant-type wearable articles use elastic elements secured in an elastically contractible condition in the waist and/or leg openings. Typically, in order to insure full elastic fit about the leg and the waist such as is provided with durable undergarments, the leg openings and waist opening are encircled at least in part with elasticized elements positioned along the periphery of the respective opening.

Pant-type wearable articles having a main body to cover the crotch region of the wearer and a separate elastic belt defining the waist opening and leg opening are known in the art, such as described in PCT Publication WO 2006/17718A. Such pant-type wearable articles may be referred to as belt-type pants. On the other hand, certain pant-type wearable articles are configured such that the outer cover of the wearable body completely covers the entirety of the garment-facing surface of the article. Such pant-type wearable articles may be referred to as uni-body pants. Belt-type pants, compared to uni-body pants, may be advantageous in having better breathability by having less layers of material in certain areas of the articles, and in that they may be manufactured economically. For belt-type pants, the elastic belt provides fit for not just the waist opening and low torso area, but also for the leg opening, in that the leg opening of belt-type pants are rendered elastic by the combination of elasticity provided by the main body and the elastic belt. Thus, for belt-type pants, sag protection and good fit for the entire article are mainly provided by the elastic belt. Providing a certain tensile stress for the elastic belt is essential for providing sag protection and good fit for the entire article. The elastic belt of belt-type pants are economically rendered elasticity by disposing a plurality of elastic strands running in the transverse direction of the article. The tensile force provided by the relatively thin elastic strands may lead to red marking of the wearer's skin. Further, the tensile force provided by the elastic strands may lead to uncomfort of the wearer.

Based on the foregoing, there is a need for a pant-type wearable article having balanced performance such as fit, comfort during wear, prevention of sagging, prevention of leakage, and prevention of red marking. There is further a need for providing such a wearable article in an economical manner.

SUMMARY OF THE INVENTION

The present intention is directed to a wearable article continuous in a longitudinal direction and a transverse direction, comprising a main body and a ring-like elastic belt comprising a front belt and a back belt, the center of the front belt is joined to a front waist panel of the main body, the center of the back belt is joined to a back waist panel of the main body, the front and back belt each having a left side panel and a right side panel where the main body does not overlap, and the transverse edges of the front belt and the back belt are joined by a seam to form a waist opening and two leg openings, wherein each of the front belt and back belt are formed by an inner sheet, an outer sheet, and a plurality of elastic bodies sandwiched therebetween and running in the transverse direction substantially parallel to each other, wherein each front belt and back belt have transversely continuous proximal and distal edges, the proximal edge being located closer than the distal edge relative to the longitudinal center of the article, each front belt and back belt having side edges, wherein:

at least some of the elastic bodies disposed on either the front belt or the back belt being arranged in at least 2 sets of a concentrated array, the concentrated array defined as meeting a), b), and c) as follows:
  a) one concentrated array is formed by 2-4 elastic bodies;
  b) each elastic body within one concentrated array is disposed in an inner-interval in the longitudinal direction between each elastic body of 2-4 mm;
  c) one specific concentrated array disposed in an extra-interval in the longitudinal direction between at least one neighboring elastic body outside the specific concentrated array of less than 8 mm and greater than the inner-interval of the specific concentrated array; wherein the entirety of the length of the belt side edge of the front belt is seamed with a certain length of the belt side edge of the back belt to define a seam length LS;

the front and back belts each divided into 4 zones extending in the transverse direction and defined by its location from the distal edge to the proximal edge relative to the percentage of the seam length LS wherein; 0-25% is the waist zone, 25-50% is the distal tummy zone, 50-85% is the proximal tummy zone, and 85-100% is the leg zone;

wherein at least 2 concentrated arrays are disposed on the front proximal tummy zone, or the back distal tummy zone.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings and which like designations are used to designate substantially identical elements, and in which:

DEFINITIONS

As used herein, the following terms shall have the meaning specified thereafter:

"Wearable article" refers to articles of wear which may be in the form of pants, taped diapers, incontinent briefs, feminine hygiene garments, and the like. The "wearable article" may be so configured to also absorb and contain various exudates such as urine, feces, and menses discharged from the body. The "wearable article" may serve as an outer cover adaptable to be joined with a separable disposable absorbent insert for providing absorbent and containment function, such as those disclosed in PCT publication WO 2011/087503A.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

"Longitudinal" refers to a direction running substantially perpendicular from a waist edge to an opposing waist edge of the article and generally parallel to the maximum linear dimension of the article.

"Transverse" refers to a direction perpendicular to the longitudinal direction.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Extendibility" and "extensible" mean that the width or length of the component in a relaxed state can be extended or increased.

"Elasticated" and "elasticized" mean that a component comprises at least a portion made of elastic material.

"Elongatable material," "extensible material," or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

DETAILED DESCRIPTION OF THE INVENTION

Figure 1:
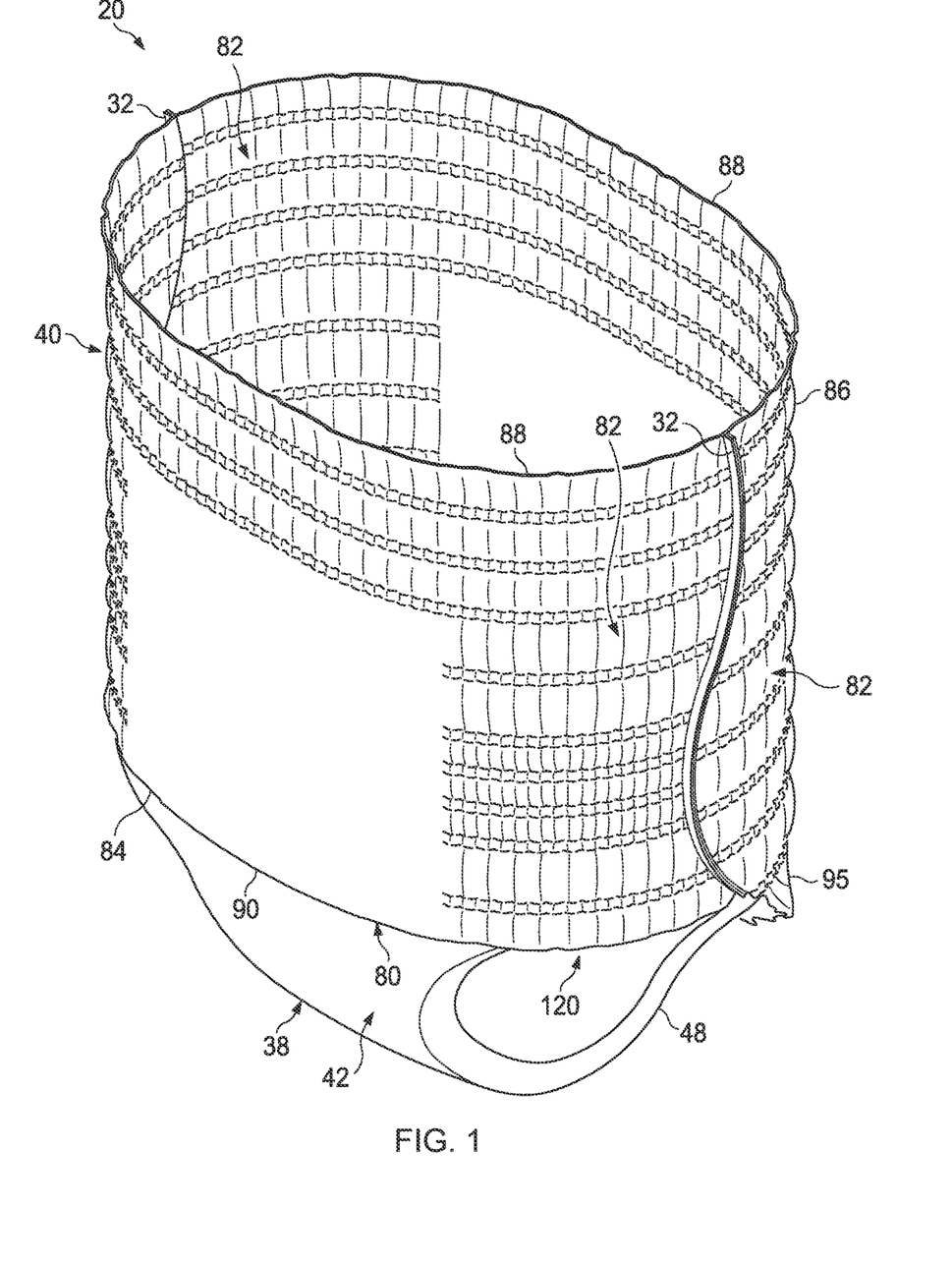
FIG. 1 is a perspective view of one embodiment of a wearable article of the present invention.
Figure 2:
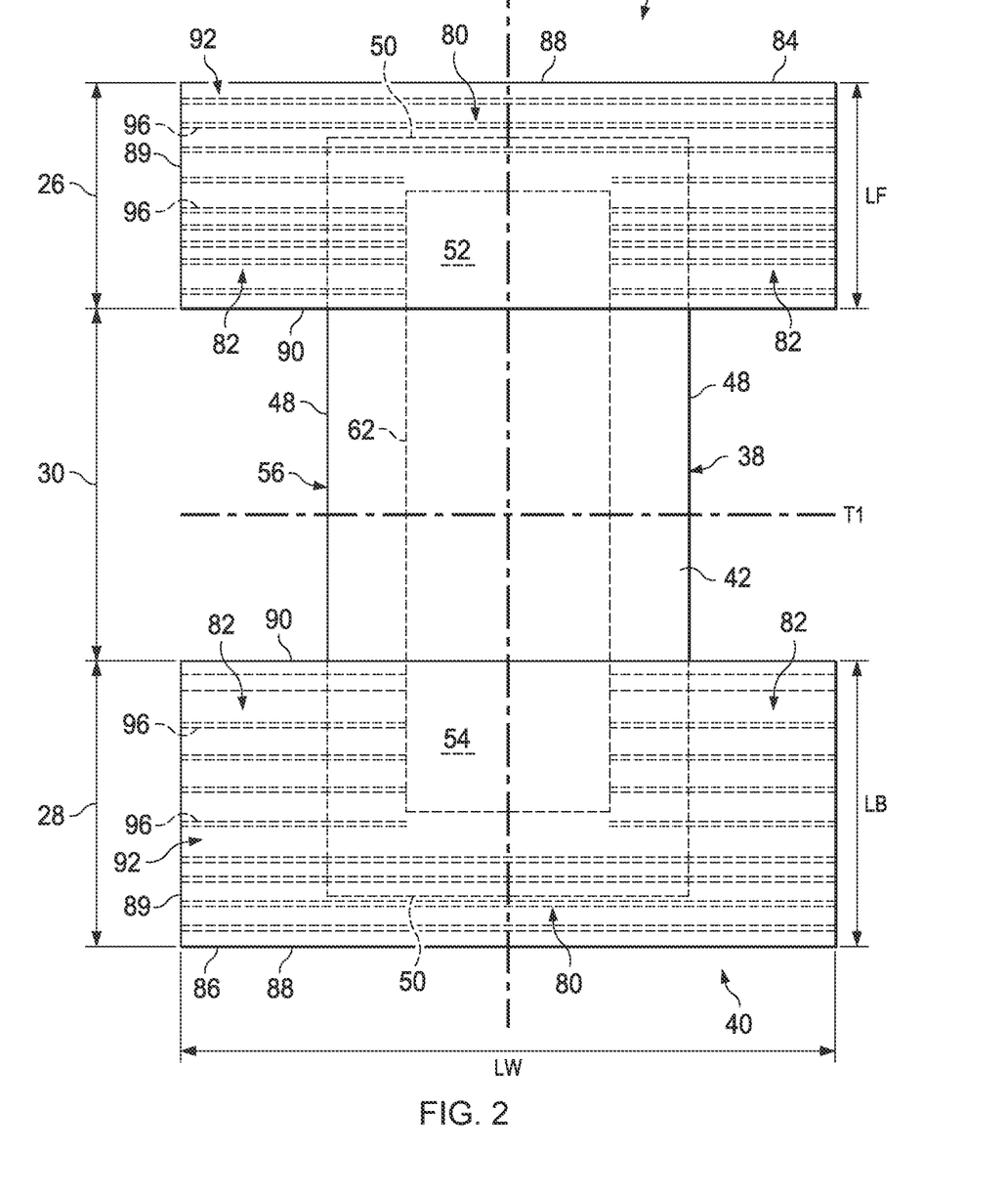
FIG. 2 is a top plan view of one embodiment of a wearable article of the present invention with the seams unjoined and removed, and in a flat uncontracted condition showing the garment facing surface.

FIG. 1 is a perspective view of an embodiment of the wearable article 20 of the present invention and FIG. 2 is a schematic plan view of the same article with the seams unjoined and in its flat uncontracted condition showing the garment-facing surface. The wearable article 20 has a longitudinal centerline L1 which also serves as the longitudinal axis, and a transverse centerline T1 which also serves as the transverse axis. The wearable article 20 has a skin-facing surface, a garment-facing surface, a front region 26, a back region 28, a crotch region 30, and seams 32 which join the front region 26 and the back region 28 to form two leg openings and a waist opening. The wearable article 20 comprises a main body 38 to cover the crotch region of the wearer, a front belt 84 and a back belt 86 (hereinafter may be referred to as "front and back belt"), the front and back belts 84, 86 forming a ring-like elastic belt 40 (hereinafter may be referred to as "waist belt") extending transversely defining the waist opening. The front and back belts 84, 86 and the main body 38 jointly define the leg openings.

The main body 38 may contain an absorbent core 62 for absorbing and containing body exudates disposed on the main body 38. In the embodiment shown in FIG. 2, the main body 38 has a generally rectangular shape, left and right longitudinally extending side edges 48 (hereinafter may be referred to as "side edge") and front and back transversely extending end edges 50 (hereinafter may be referred to as "end edge"). The main body 38 also has a front waist panel 52 positioned in the front region 26 of the wearable article 20, a back waist panel 54 positioned in the back region 28, and a crotch panel 56 between the front and back waist panels 52, 54 in the crotch region 30. The center of the front belt 84 is joined to a front waist panel 52 of the main body 38, the center of the back belt 86 is joined to a back waist panel 54 of the main body 38, the front and back belt 84, 86 each having a left side panel and a right side panel 82 where the main body 38 does not overlap.

Referring to FIGS. 1 and 2, the ring-like belt 40 formed by the front belt 84 and back belt 86 acts to dynamically create fitment forces and to distribute the forces dynamically generated during wear. Herein, the term "proximal" is used to indicate the position of a "proximal" portion being closer relative to the longitudinal center of the article, also closer relative to the crotch panel 56 of the main body 38 than the position of a "distal" portion. Therefore, the proximal edge 90 is located closer than the distal edge 88 relative to the crotch panel 56 of the main body 38. The front and back belts 84, 86 may be joined with each other only at the side edges 89 at the seams 32 to form a wearable article having a waist opening and two leg openings. Each leg opening may be provided with elasticity around the perimeter of the leg opening by the combination of elasticity from the front belt 84, the back belt 86, and any from the main body 38. The front leg opening region 120 is disposed adjacent the leg opening along the proximal edge 90 of the left and right side panels 82 of the front belt 84.

The front and back belts 84, 86 are discontinuous with one another in the crotch region 30. In such embodiment, there is no material that covers the entirety of either the wearer-facing surface or garment-facing surface of the article. The front central panel 80 may partly overlap with the front waist panel 52 of the main body 38. The back central panel 80 may partly overlap with the back waist panel 54 of the main body 38. However, the central panels 80 may not extend into the crotch panel 56 of the main body 38 and not be disposed in the crotch panel 56. In the embodiment shown in FIG. 2, the central panels 80 partly overlap with and are joined to the front waist panel 52 and the back waist panel 54, respectively.

Referring to FIG. 2, the front belt 84 and back belt 86 may each comprise an inner sheet 94, an outer sheet 92, (hereinafter also collectively "belt sheets") and configured to impart elasticity per each zone according to the relationship described below. (The inner sheet 94 is not shown.) Each of the front and back belts 84, 86 may be made as a laminate having a plurality of belt elastic bodies 96 sandwiched between the inner and outer sheets 94, 92. In one embodiment, the belt elastic bodies 96 extend in the transverse direction to provide a ring-like elastic belt when the front belt 84 and the back belt 86 are joined. In one embodiment, at least some of the elastic bodies 96 extend in the transverse direction parallel to each other. In one embodiment, all of the elastic bodies 96 extend in the transverse direction substantially parallel to each other. Such an article may be economically made.

In one embodiment, the effective transverse width LW of the back belt 86 in the uncontracted condition may be the same as the transverse width of the front belt 84 of the same condition. By "effective transverse width", what is meant is the width available for forming the wear-facing surface of the article. In one embodiment, each of the proximal edges 90 and the distal edges 88 of the front belt 84 and the back belt 86 may be substantially parallel, as in FIG. 2.

In one embodiment, the longitudinal length LB of the back belt 86 between the back distal edge 88 and the back proximal edge 90 along its entire width LW of the back belt 86 may be approximately the same as the longitudinal length LF of the front belt 84 between the front distal edge 88 and the front proximal edge 90. In such embodiment, the seams 32 close the front and back belt 84, 86 side edges 89 of the same length for forming the article. Such an article may be economically made.

In one embodiment, the back belt 86 may have a greater longitudinal length LB between the back distal edge 88 and the back proximal edge 90 along its entire width LW of the back belt 86 in the transverse direction than the longitudinal length LF of the front belt 84 between the front distal edge 88 and the front proximal edge 90 (FIGS. 1-4). In such embodiment, when the wearable article is assembled to form the waist opening and the leg openings, the wearable article 20 is folded along the transverse centerline T1 such that the front distal edge 88 is aligned with the back distal edge 88. The front side edge 89 is also aligned with a portion of the back side edge 89. Then the front belt 84 and the back belt 86 are joined at the front and back side edges 89 at the seams 32. The front and back proximal edges 90, however, may not be aligned to one another. The back proximal edge 90 may be disposed longitudinally closer than the front proximal edge 90 relative to the transverse center line T1 such that the proximal portion of the back side panel 82 extends toward the crotch panel 56 of the main body 38 beyond the front proximal edge 90. The side edge of the proximal portion of the back side panel 82 may not be joined to anywhere and free from attachment. Thus, the proximal portion of the back side panel 82 provides a buttock cover 95 as in FIG. 1.

Figure 3:
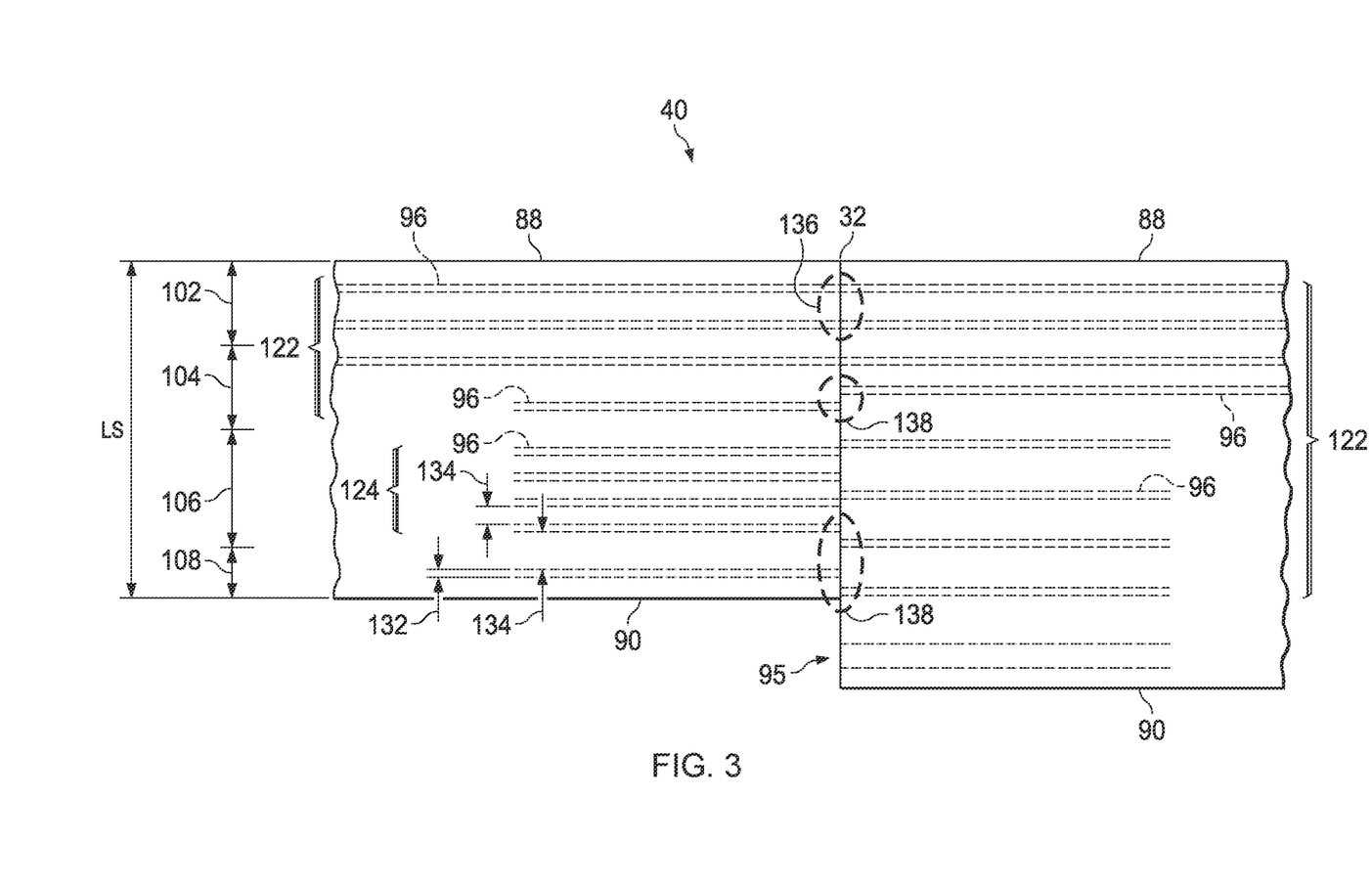
FIG. 3 is a side plan view of one embodiment of a wearable article of the present invention in a flat uncontracted condition showing the garment facing surface.

Whether or not the longitudinal length LB of the back belt 86 and the longitudinal length LF of the front belt 84 are the same, the entirety of the longitudinal length LF of the belt side edge 89F of the front belt 84 is seamed with the belt side edge 89B of the back belt 86 to define a seam length LS, as in FIG. 3. When the front belt 84 has straight distal edges 88 and proximal edges 90 that are substantially parallel of each other, then the longitudinal length LF of the front belt 84 is equal to the seam length LS.

In one embodiment, the outer sheet 92 of the front or back belt 84, 86 towards the distal edge 88 may be longer than the size of the inner sheet 94 in the longitudinal direction, and an end flap of the outer sheet 92 may be folded over the distal end of the inner sheet 94 at the waist opening. The front and back belts 84, 86 may be provided in low caliper non-woven material for sake of breathability and softness of the belt 40.

The tensile stress (N/m) of the front and back elastic belts 84, 86, respectively, may be profiled in order to provide the benefits of the present invention. The tensile stress may be measured, for example, by the Belt Zone Tensile Stress Measurement described herein below. When the elasticity of the front and back elastic belts 84, 86 are provided by a plurality of elastic bodies 96 running in the transverse direction, the tensile stress may be adjusted by one or more of the following methods; 1) elongation rate of the elastic body 96; 2) density (dtex) of the elastic body 96; 3) longitudinal interval of multiple elastic bodies 96; and 4) effective length of elasticity of the elastic body 96 in the transverse direction. By elongation, "0% elongation" is meant the original length of the elastic body. When a portion of an elastic body is removed of its elasticity, the remainder of the intact elastic body capable of imparting elasticity is defined as the "effective length of elasticity of an elastic body". The elastic bodies 96 disposed on the front and/or back belt 84, 86 may be treated such that certain of the area overlapping the front and/or back waist panels 52, 54 of the main body 38 are removed of elasticity. Removal of elasticity from at least a portion of the area overlapping the front and/or back waist panel 52, 54 of at least one elastic body may be advantageous when the main body 38 comprises an absorbent core 62, in that elasticity in the front and/or back area may cause bunching of the absorbent core 62 and interfere with close fit of the main body 38 to the wearer. In one embodiment, at least a portion of, or at least 10% of, or at least 20% of, or at least 30% of, the elasticity of; at least one of, or at least half of, or at least two thirds of, or all of, the elastic bodies are removed in the region overlapping with the front and back waist panels 52, 54 or the absorbent core 62 of the main body 38.

Referring to FIG. 3, the elastic bodies 96 of the belt 40 of the present invention may be arranged in arrays. The arrays of the present invention, whether basic array 122 or concentrated array 124, have at least 2 elastic bodies 96 disposed in close proximity to each other in the longitudinal direction. Specifically, a plurality of elastic bodies 96 are disposed at an interval, herein defined as an inner-interval 132, of 2-4 mm. Any two or more elastic bodies 96 disposed in an inner-interval 132 of 2-4 mm are referred to herein as an array. Without being bound by theory, by disposing the elastic bodies 96 in such close proximity to each other, the array exhibits a behavior as if it were one elastic body with a certain width, and provides various benefits. For example, the array provides more or less the combined tensile force of the elastic bodies 96 in the array, such that each elastic body 96 may be disposed at a much lower tensile force. Further, the gathers created in the inner-interval 132 of the array are so fine that the area of the inner sheet 94 facing the wearer is significantly increased. Such increased area of material in the inner-interval 132, combined with the elastic bodies 96 of the array, apply a tensile force to the wearer over a distributed width, compared to the width of a single elastic body. Namely, the array exhibits a behavior as if it were one elastic body. As such, the array may provide a good fit to the wearer by using relatively low density elastic bodies which are economically supplied. The reduction of tensile force in a concentrated area compared to that of a single elastic body, may also reduce red marking on the skin of the wearer, and provide the wearer with a more comfortable and soft fit. Further, an array may provide the appearance of an elastic body of a certain width, similar to elastic bodies disposed on a durable undergarment. Thus, disposal of an array may connote an undergarment look, or high quality.

Herein, the basic array 122 comprises 2-10 elastic bodies, or 2-5 elastic bodies, or 2-3 elastic bodies. Herein, the concentrated array 124 comprises 2-4 elastic bodies, or 2-3 elastic bodies. The basic array 122 may be disposed in a relatively large extra-interval 134 in the longitudinal direction between at least one neighboring elastic body outside the array, of 8-22 mm. The concentrated array 124 may be disposed in a relatively small extra-interval 134 in the longitudinal direction between at least one neighboring elastic body outside the array of less than 8 mm, or from 4 to less than 8 mm; wherein the extra-interval 134 is greater than the inner-interval 132.

In summary, an array may be defined as meeting a), b), and c) as follows:
 a) one array is formed by 2-10 elastic bodies;
 b) each elastic body within one array is disposed in an inner-interval 132 in the longitudinal direction between each elastic body of 2-4 mm;
 c) one specific array disposed in an extra-interval 134 in the longitudinal direction between at least one neighboring elastic bodies outside the specific array of greater than the inner-interval 132.

In summary, a basic array 122 may be defined as meeting a), b), and c) as follows:
 a) one basic array 122 is formed by 2-10 elastic bodies;
 b) each elastic body within one basic array 122 is disposed in an inner-interval 132 in the longitudinal direction between each elastic body of 2-4 mm;
 c) one specific basic array 122 disposed in an extra-interval 134 in the longitudinal direction between at least one neighboring elastic body outside the specific basic array 122 of 8-22 mm;

In summary, a concentrated array 124 may be defined as meeting a), b), and c) as follows:
 a) one concentrated array 124 is formed by 2-4 elastic bodies;
 b) each elastic body within one concentrated array 124 is disposed in an inner-interval 132 in the longitudinal direction between each elastic body of 2-4 mm;
 c) one specific concentrated array 124 disposed in an extra-interval 134 in the longitudinal direction between at least one neighboring elastic body outside the specific concentrated array 124 of greater than the inner-interval 132 of the specific concentrated array 124 and less than 8 mm.

The front belt 84 may comprise at least 5 arrays. The front belt 84 may comprise at least 1, or at least 2, or at least 3, or at least 4 basic arrays 122. The elastic bodies disposed on the front belt 84 may all be arranged in arrays. The front belt 84 may comprise basic arrays 122 and concentrated arrays 124. The elastic bodies disposed on the front belt 84 may all be arranged in either basic arrays 122 or concentrated arrays 124.

The back belt 86 may comprise at least 5 arrays. The back belt 86 may comprise at least 1, or at least 2, or at least 3, or at least 4 basic arrays 122. The elastic bodies disposed on the back belt 86 may all be arranged in arrays. The back belt 86 may comprise basic arrays 122 and concentrated arrays 124. The elastic bodies disposed on the back belt 86 may all be arranged in basic arrays 122.

Referring again to FIG. 3, arrays may be disposed on both the front belt 84 and the back belt 86. The arrays from the front and back belt 84, 86 may be disposed in a matched arrangement 136. By matched arrangement 136, what is meant is that at least one elastic body comprised in an array at the belt side edge 89 of the front belt 84 and at least one elastic body comprised in an array at the belt side edge 89 of the back belt 86 are located in substantially the same position at both seams 32. By substantially same position, what is meant is a position within reasonable deviation from the designed arrangement occurred in high speed production of the article, for example within 4 mm, or within 2 mm. In one embodiment, all of the elastic bodies comprised in an array at the belt side edge 89 of the front belt 84 and all of the elastic bodies comprised in an array at the belt side edge 89 of the back belt 86 may be located in substantially the same position at both seams 32. In embodiments where the distal edges 88 of the front and back belts 84, 86 are substantially parallel and matched, and also all of the elastic bodies 96 extend in the transverse direction substantially parallel to each other such as in FIGS. 2-4, a matched arrangement may alternatively be identified by comparing the position of the array located from the distal edge 88 of the belt. When the positions of the arrays from the distal edge 88 in the front and back belt 84, 86 match, then this is considered a matched arrangement.

Matched arrangements 136 may be formed by either basic arrays 122 or concentrated arrays 124. Matched arrangements 136 of arrays may be useful for providing clearly defined gathers in the extra-interval 134, such as in the vicinity of the waist opening or the leg opening. The area indicated as 136 in FIG. 3 is considered to include 2 matched arrangements 136.

Still referring to FIG. 3, when there are at least 3 basic arrays disposed on the article, the arrays may be disposed in a certain location in the longitudinal direction such that the arrays are in an alternate arrangement 138. By alternate arrangement 138, what is meant is an arrangement of either e) or f) as follows:
  e) the belt side edge 89 of one specific basic array comprised in the front belt 84 is located in the extra-interval 134 of two basic arrays of the back belt 86 at the belt side edge 89;
  f) the belt side edge 89 of one specific basic array comprised in the back belt 86 is located in the extra-interval 134 of two basic arrays of the front belt 84 at the belt side edge 89.

There may be more than one, for example 2 or 3, specific basic arrays comprised in either the front or back belt 84, 86 at the belt side edge 89 being located in the extra-interval 134 of two arrays comprised in the other side belt at the belt side edge 89.

Namely, at both seams 32, an alternate arrangement is identified when at least one basic array 122 at the belt side edge 89 of one of the front or back belt 84, 86 is located in the extra-interval 134 of 2 basic arrays 122 at the belt side edge 89 of the other front or back belt 84, 86. Alternate arrangements 138 of basic arrays 122 may be useful for providing a soft fit around the side seam 32 by distributing the forces provided by the basic arrays 122 disposed on the front belt and the back belt 84, 86. There are two areas indicated as 138 in FIG. 3. The two areas indicated as 138 are considered to include a total of 5 alternate arrangements 138. The article of the present invention may have at least 2, or at least 3 alternate arrangements 138.

As described above, the basic array 122 or concentrated array 124 of the present invention may provide more or less the combined tensile force of the elastic bodies 96 in the array, such that each elastic body 96 may be disposed at a relatively lower tensile force. Accordingly, the elastic bodies 96 for forming a basic array 122 may have a density of no more than 940 dtex, and disposed at an elongation of from 100% to 350%, or from 150% to 300%. By elongation, "0% elongation" is meant the original length of the elastic body. The elastic bodies 96 for forming a concentrated array 124 may have a density of no more than 1100 dtex, or no more than 940 dtex, and disposed at an elongation of from 150% to 300%.

In one embodiment, the total number of elastic bodies 96 disposed on a single article may be limited for providing the article in an economical manner. The belt of the present invention may be disposed of a total of no more than 60, or no more than 54, or no more than 46 elastic bodies. The article of the present invention may have an entire longitudinal length of the article of from 350 mm to 600 mm, an effective transverse belt width (LW) of from 315 mm to 500 mm, a back belt longitudinal length (LB) of from 100 mm to 180 mm, a front belt longitudinal length (LF) of from 80 mm to 160 mm, a main body longitudinal length of from 310 mm to 560 mm, and a main body transverse width of from 150 mm to 210 mm. The article of the present invention may have a distance between the distal edge of the front belt to the longitudinal edge of the main body of from 0 mm to 70 mm, and a distance between the distal edge of the back belt to the longitudinal edge of the main body of from 0 mm to 90 mm, and such distances on the front and back belt may be the same or different. The longitudinal length of the main body may be from 70% to 100% of the entire longitudinal length of the article. When the main body comprises an absorbent core 62, the core may have a longitudinal length of from 270 mm to 500 mm, a maximum transverse width of the core of from 90 mm to 125 mm, and a distance between the longitudinal edge of the core to the longitudinal edge of the main body of from 10 mm to 40 mm. The longitudinal length of the core may be from 60% to 95% of the entire longitudinal length of the article, or from 66% to 97% of the main body. The article of the present invention may have a Waist Circumference Force provided by the elastic bodies 96 disposed on the waist belt 40 of no more than 10N, or no more than 8N, according to the Whole Article Force Measurement as described herein below. The Whole Article Force Measurement is for quantifying the force provided by the article 20 when stretched along the waist circumference, simulating initial stretch experience of the article 20 in the transverse direction when the user inserts hands in the article and expands the article. Namely, more or less the total tensile force provided by the elastic bodies 96 disposed in the transverse direction are measured. While there may be other elastic bodies disposed on the article, for example along the longitudinal side edges of the main body, the impact of such other elastic bodies are known to be small, when the user stretches the article in the transverse direction. The Whole Article Force Measurement is obtained by extending, or loading, the article in the transverse direction until a force of 19.6N is attained, wherein the force at the point where the belt 40 article reaches 70% of the maximum stretch is obtained. The force expected to be perceived by the user for expanding the article may be controlled, such that the user may experience a satisfying expansion of the belt 40 without excess effort.

Figure 4:
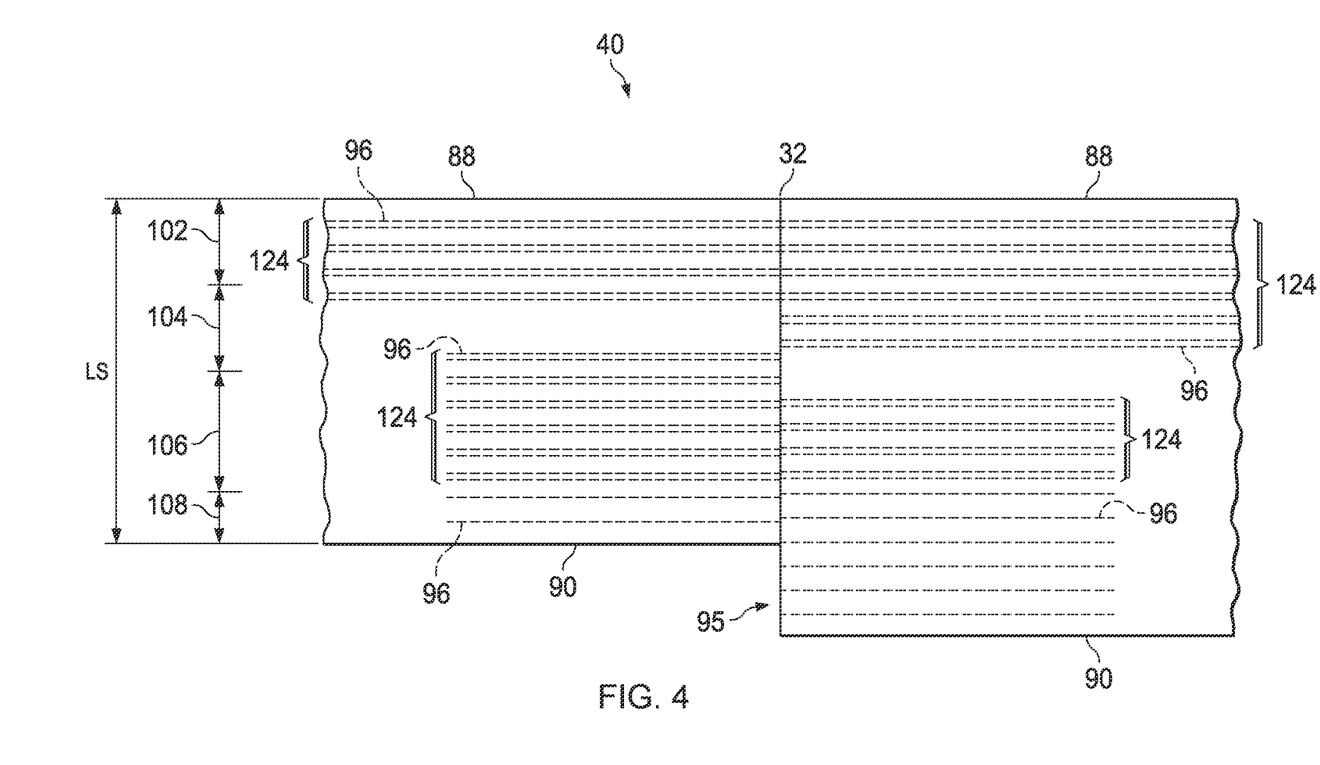
FIG. 4 is a side plan view of another embodiment of a wearable article of the present invention in a flat uncontracted condition showing the garment facing surface.

Elastic bodies arranged in basic arrays 122, concentrated arrays 124, or otherwise, may be disposed in combination in different zones of the elastic belt for creating areas of higher and lower tensile stress. Referring to FIGS. 3-4, the front and back belts 84, 86 are each divided into 4 zones extending in the transverse direction and defined of its position from the distal edge 88 to the proximal edge 90 relative to the percentage of the seam length LS. The entirety of the length of the belt side edge 89 of the front belt 84 is seamed with a certain length of the belt side edge 89 of the back belt 86 to define a seam length LS. When seam length LS is considered 0% at the distal edge 88 and 100% at the proximal edge 90 of the front belt 84, the zones are defined as such: 0-25% is the waist zone 102, 25-50% is the distal tummy zone 104, 50-85% is the proximal tummy zone 106, and 85-100% is the leg zone 108. When there is an elastic body disposed at 25% from the distal edge 88, such elastic body is considered to be included in the waist zone 102. When there is an elastic body disposed at 50% from the distal edge 88, or 85% from the distal edge 88, such elastic body is considered to be included in the proximal tummy zone 106. For embodiments where the back belt 86 has a greater longitudinal length LB than the longitudinal length LF of the front belt 84, the remaining length of "LB minus LS" of the back belt 86 is not counted in the 4 zones described above.

Referring to FIG. 3, at least one alternate arrangement 138 may be located in at least one of the distal tummy zone 104, the proximal tummy zone 106, and the leg zone 108. At least one matched arrangement 136 may be located in at least one of the waist zone 102 and the leg zone 108. The waist zone 102 may comprise at least one matched arrangement 136, the distal tummy zone 104 may comprise at least one alternate arrangement 138, the proximal tummy zone 106 may comprise at least one alternate arrangement 138, and the leg zone 108 may comprise at least one matched arrangement 136. All of the elastic bodies 96 disposed on the waist zone 102 may be in a matched arrangement 136, and all of the elastic bodies 96 disposed on the distal tummy zone 104 may be in an alternate arrangement 138.

In one embodiment, concentrated arrays 124 may be disposed in zones for which higher tensile stress is desired. Disposal of at least 2 concentrated arrays 124 may be particularly effective. Referring to FIGS. 3-4, at least 2 concentrated arrays 124 may be disposed on the front proximal tummy zone 106. The tensile stress of the front proximal tummy zone 106 may be provided higher than the tensile stress of any other zone. Referring to FIG. 4, at least 2 concentrated arrays 124 may be disposed on the back distal tummy zone 104. The tensile stress of the front leg zone 108 may be no more than 50% of the tensile stress of the front proximal tummy zone 106, and the tensile stress of the back leg zone 108 may be no more than 100% of the tensile stress of the back proximal tummy zone 106. The tensile stress of the back distal tummy zone 106 may be higher than the tensile stress of the front distal tummy zone 106.

Figure 5:
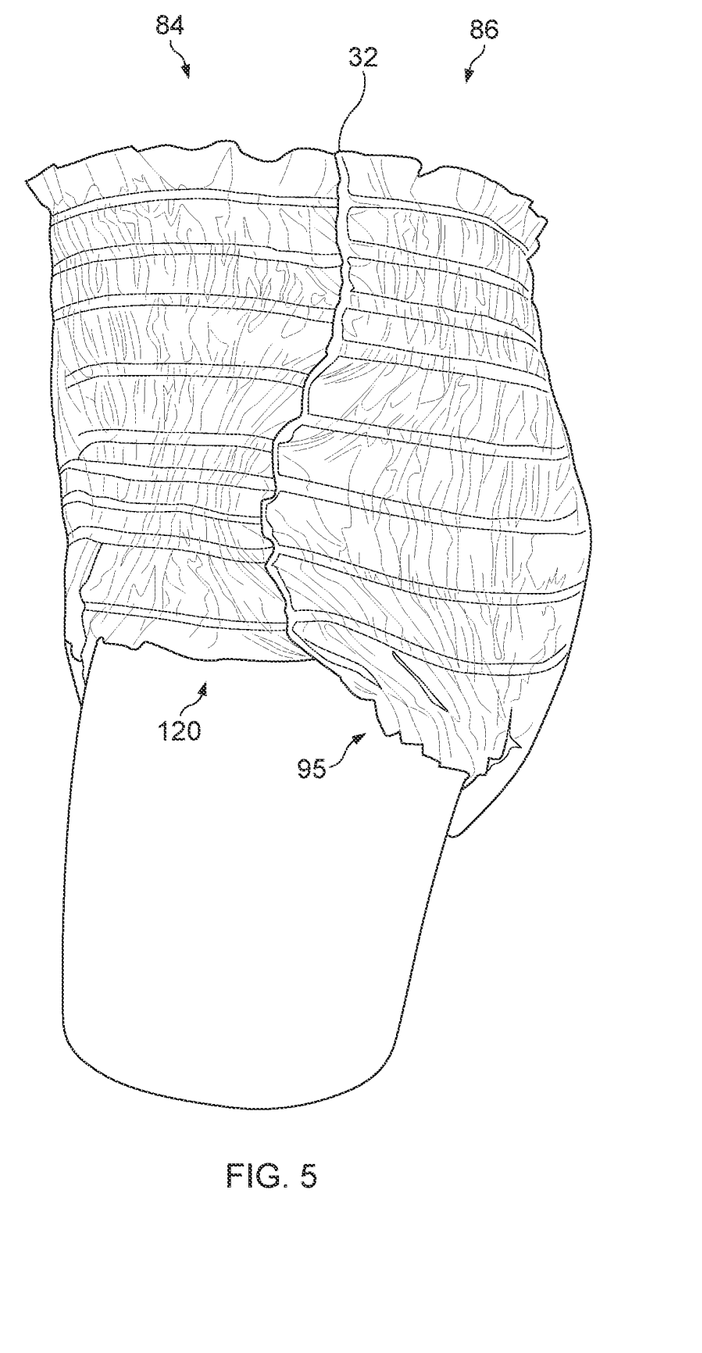
FIG. 5 is a side view of one embodiment of a wearable article of the present invention worn on a mannequin.
Figure 6:
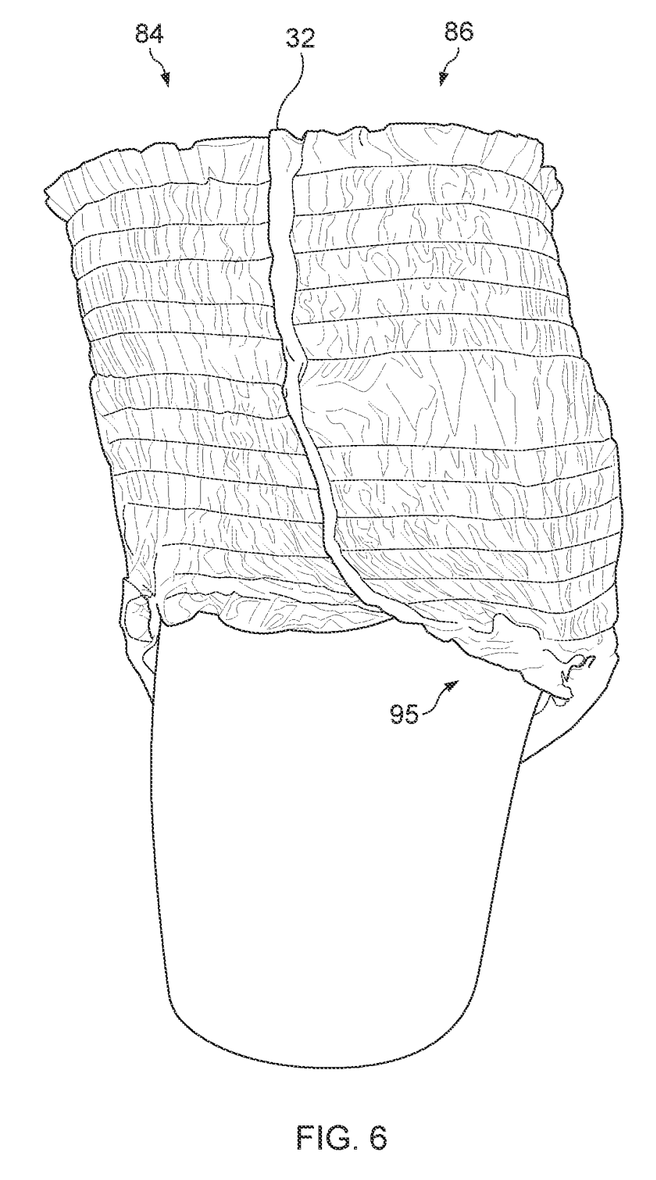
FIG. 6 is a side view of a wearable article of the prior art worn on a mannequin.

The profiling and arrangement of elastic bodies 96 of FIGS. 3-4 may provide the article of the present invention to take an S-curve side seam 32 observed by the side when worn by the wearer, as shown as in FIG. 5. Such behavior of the waist belt of the present invention is in contrast with many belt-type wearable articles available in the market as shown in FIG. 6, wherein the side seam takes a relatively straight line, or a line slightly slanted toward the back. Without being bound by theory, the aforementioned profiling of the elastic bodies per zone is believed to provide the article of the present invention with a shaped waist belt that conforms well to a human body, particularly to a lower torso of a child of less than 36 months of age, and therefore provides good fit and comfort to the wearer, without compromise of sagging prevention or leakage prevention. In one embodiment, the front proximal tummy zone may be subject to high tensile stress by disposing at least 2 concentrated arrays 124, such that the article may be anchored against the wearer's trochanter. In one embodiment, the back distal tummy zone may be subject to higher tensile stress by disposing at least 2 concentrated arrays 124 than the front distal tummy zone 106, for accommodating the wearer's front waist area.

In one embodiment, concentrated arrays 124 may be disposed in zones for which higher tensile stress is desired, and for further providing an aesthetic effect. As described above, an array may provide the appearance of an elastic body of a certain width, similar to elastic bodies disposed on a durable undergarment. At least 2 concentrated arrays 124 may be disposed in each on the front waist zone 102 and the back waist zone 102 to provide the appearance of a waist band. These at least 2 concentrated arrays 124 from the front waist zone 102 and the back waist zone 102 may be disposed in a matched arrangement 136. At least 2 concentrated arrays 124 may also be disposed on the front leg zone 108 to provide the appearance of a leg band (not shown).

Whole Article Force Measurement

Force is measured using an Electronic Tensile Tester with a computer interface such as the MTS Criterion C42 running TestWorks 4 Software (available from MTS SYSTEMS (CHINA) CO., LTD) or equivalent instrument. A load cell is selected so that force results for the samples tested will be between 10 and 90% of capacity of the load cell used. The instrument is calibrated according to the manufacturer's instructions. All testing is performed in a room maintained at 23±2° C. and 50±5% relative humidity.

Figure 7:
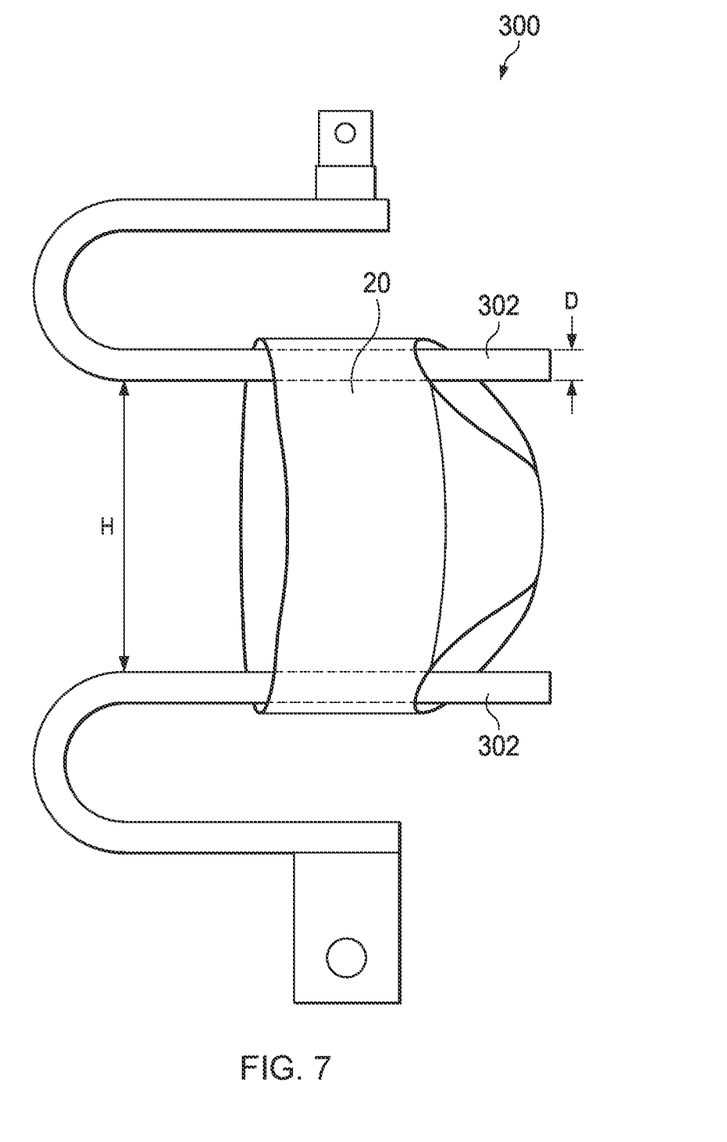
FIG. 7 is a schematic view of an example of a hanger-type sample holding fixture according to the "Whole Article Force Measurement".

The tensile tester is fitted with hanger-type sample holding fixtures 300 as shown in FIG. 7. Each fixture comprises a rigid linear rubber-coated horizontal bar section 302 to prevent sample slippage during testing. The outer bar diameter (including the rubber coating) of the horizontal bar sections is 10.0 mm. The central axes of the horizontal bar sections 302 are configured to remain parallel and in the same vertical plane throughout the test procedure. The gauge circumference is determined by the following equation:

$$\text{Gauge Circumference} = 2 \times (H + D + \pi D/2)$$

where H is the vertical gap between the horizontal bar sections 302, and D is the outer diameter of the bar.

The instrument is set up to go through the following steps:

| | |
|---|---|
| Crosshead Speed | 254.0 mm/min |
| Final Load Point | 19.61N |
| Hold Time | 0 |
| Number of Cycles | 1 |
| Data Acquisition Rate | 50 Hz |

A sample article 20 is inserted onto the upper horizontal bar section 302 so that the bar passes through the waist opening and one leg opening of the article. The crosshead is raised until the specimen hangs above the lower bar and does not touch lower bar 302. The load cell is tared and the crosshead is lowered to enable the lower bar 302 to be inserted through the waist opening and other leg opening without stretching the article. The article is adjusted so that the longitudinal centerline L1 of the article is in a horizontal plane halfway between the upper and lower bars 302. The center of the side portion in contact with the bar 302 is situated on the same vertical axis as the instrument load cell. The crosshead is raised slowly while the article is held in place by hand as necessary until the force is between 0.05 and 0.1N, while taking care not to add any unnecessary force. The gauge circumference at this point is the Initial Gauge Circumference. The test is initiated and the crosshead moves up at 254 mm/min until a force of 19.6N is attained, then the crosshead immediately returns to the initial gauge circumference at the same speed. The maximum circumference at 19.6N and the force at 70% stretch circumference during the extension segment of the test are recorded.

$$\text{Circumference(mm)} = 2 \times (H + D + \pi D/2)$$

The maximum circumference at 19.6N is defined as the Full Stretch Circumference (mm). The 70% stretch circumference is defined as the full stretch circumference×0.7. The Waist Circumference Force is defined as the force at 70% stretch circumference during the load (extension) segment of the test.

Five samples are analyzed and their average Initial Gauge Circumference, average Full Stretch Circumference and average Waist Circumference Force are calculated and reported to the nearest 1 mm, 1 mm and 0.01 N, respectively.

Belt Zone Tensile Stress Measurement

The tensile stress (N/m) is calculated by tensile force (N) divided by the specimen width (m). Force may be measured using an Electronic Tensile Tester with a computer interface such as the MTS Criterion C42 running TestWorks 4 Software (available from MTS SYSTEMS (CHINA) CO., LTD) or equivalent instrument. A load cell is chosen so that force results for the samples tested will be between 10 and 90% of capacity of the load cell. The instrument is calibrated according to the manufacturer's instructions. All testing is performed in a room maintained at 23±2° C. and 50±5% relative humidity. The instrument is equipped with single line contact grips at least as wide as the test specimen.

To obtain test specimens, the sample article is cut open along the side seams 32, and the front and rear elastic belt sections 40 are removed from the main body 38 by separating the bonding between the waist belt and main body. Cold Spray may be used, paying attention not to make wrinkles in the belt sections. Care is taken not to spray on any belt elastic body 96. The obtained elastic belts 40 are severed into zones 102, 104, 106, 108 according to the present invention with care not to cut any elastic body 96. Samples are pre-conditioned at 23° C.±2 C.° and 50%±5% relative humidity for two hours prior to testing.

The instrument is set up to go through the following steps. Initial Gauge Length is calculated from the Initial Gauge Circumference which is determined during the Whole Article Force Test using separate identical articles, as described above. Initial Gauge Length=0.5×Initial Gauge Circumference. The final gauge length is calculated from the Full Stretch Circumference which is determined during the Whole Article Force Test, as described above.

| | |
|---|---|
| Crosshead Speed | 254.0 mm/min |
| Data Acquisition Rate | 50 Hz |
| Final Gauge Length | 0.5 × Full Stretch Circumference |
| Hold Time | 0 |
| Number of Cycles | 1 |

One end of the specimen is clamped into the upper clamp and the load is tared. The other end of the specimen is clamped into the lower clamp. Approximately 5 mm of each end of the specimen is behind the contact line of the grip. The test is started and the specimen is extended to the final gauge length at a crosshead speed of 254 mm/min, then immediately returned to the original gauge length at the same speed. The specimen is extended in the article transverse direction during the test. The unload force at 70% of the Final Gauge Length during the unload segments of the test is recorded.

Five articles are analyzed and the unload forces are recorded for each of the front and back zones 102, 104, 106, 108. The average tensile force (N) is calculated to the nearest 0.01 N for each zone including the front and back specimens for that zone. The tensile stress for each zone is calculated by the average tensile force (N) divided by the average specimen width (m) and reported to the nearest 0.1 N/m.

EXAMPLES

Example 1

A wearable article of the present invention having an elastic profiling according to FIGS. 2, 3, and Table 1 below having an effective belt width LW of 355 mm and a seam length LS of 130 mm.

Example 2

A wearable article of the present invention having an elastic profiling according to FIG. 4, and Table 1 below having an effective belt width LW of 355 mm and a seam length LS of 130 mm.

Comparative Example 1

Figure 8:
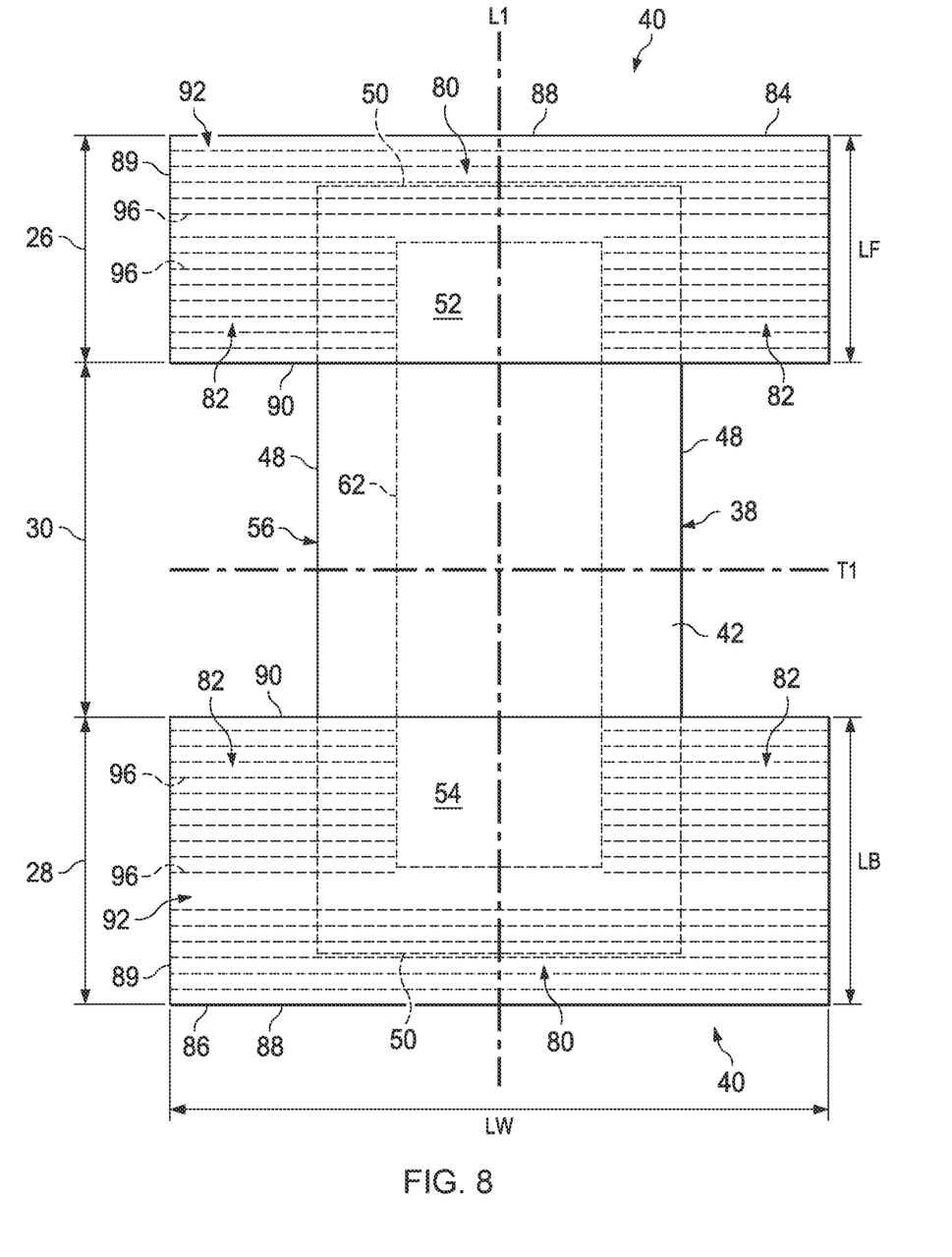
FIG. 8 is a top plan view of one embodiment of a wearable article of the prior art with the seams unjoined and removed, and in a flat uncontracted condition showing the garment facing surface.
Figure 9:
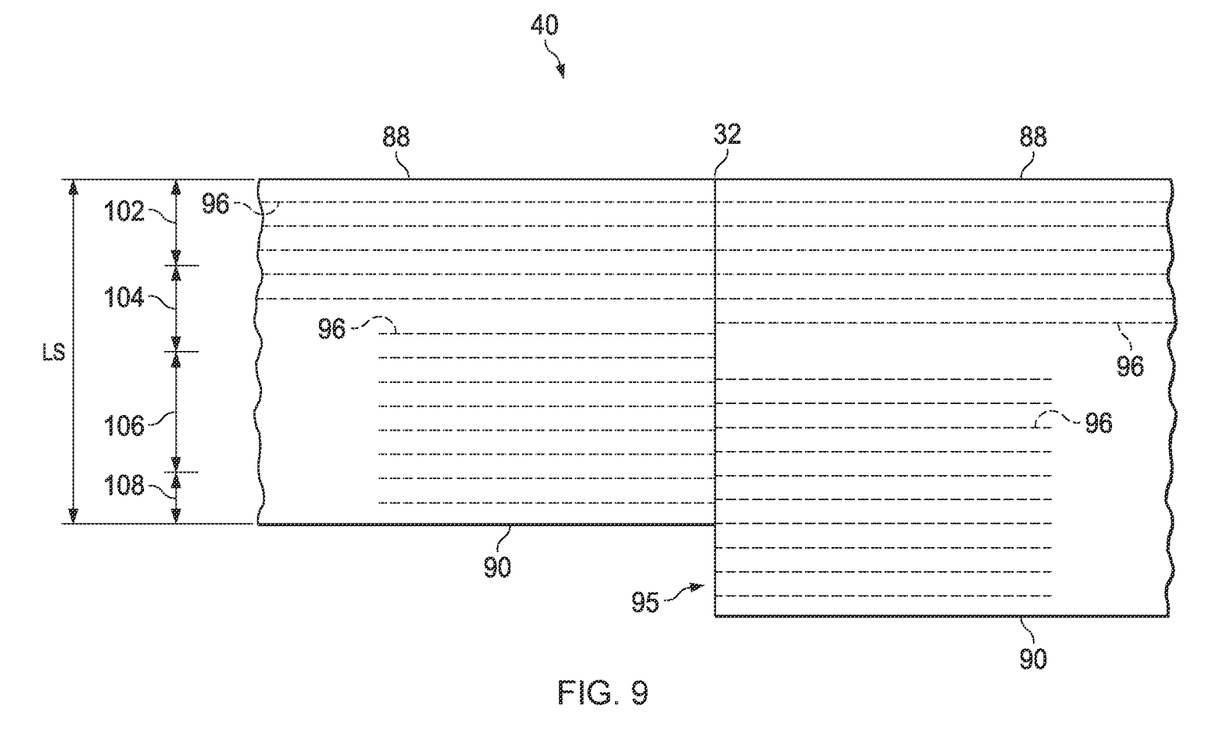
FIG. 9 is a side plan view of one embodiment of a wearable article of the prior art in a flat uncontracted condition showing the garment facing surface.

A wearable article of the prior art having an elastic profiling according to FIGS. 8, 9, and Table 1 below having an effective belt width LW of 355 mm and a seam length LS of 130 mm.

TABLE 1

| | dtex/elongation %/number of elastic bodies | | |
|---|---|---|---|
| | Example 1 | Example 2 | Comparative Example 1 |
| Front waist zone | 540dtex/170%/4 | 940dtex/210%/3 | 940dtex/210%/3 |
| Front distal tummy zone | 540dtex/170%/2 and 540dtex/275%/2 with tummy cut | 540dtex/180%/2 and 540dtex/180%/2 with tummy cut and 540dtex/275%/1 with tummy cut | 940dtex/210%/3 and 680dtex/275%/1 with tummy cut |
| Front proximal tummy zone | 540dtex/275%/2 with tummy cut and 940dtex/275%/6 with tummy cut | 540dtex/275%/1 with tummy cut and 940dtex/275%/6 with tummy cut | 680dtex/275%/5 with tummy cut |
| Front leg zone | 540dtex/275%/2 with tummy cut | 540dtex/150%/4 with tummy cut | 680dtex/275%/2 with tummy cut |
| Back waist zone | 540dtex/170%/4 | 940dtex/210%/3 | 940dtex/210%/3 |
| Back distal tummy zone | 940dtex/170%/4 | 1100dtex/180%/3 | 1100dtex/170%/3 |
| Back proximal tummy zone | 540dtex/275%/6 with tummy cut | 1100dtex/180%/1 and 540dtex/275%/4 with tummy cut | 680dtex/275%/4 with tummy cut |
| Back leg zone | 540dtex/275%/2 with tummy cut | 540dtex/150%/2 with tummy cut | 680dtex/275%/3 with tummy cut |

Elastic bodies indicated as "tummy cut" are removed of elasticity at the central area of the central panels 80 overlapping with the main body 38, and have 66% effective length of elasticity.

The Waist Circumference Force and tensile stress for each zone were measured according to the Whole Article Force Measurement and Belt Zone Tensile Stress Force Measurement methods herein, respectively, for Example 1 and Comparative Example 1. Results are found in Table 2.

TABLE 2

| | Example 1 | Comparative Example 1 |
|---|---|---|
| Waist Circumference Force (N) | 6.12 | 5.99 |
| Tensile Stress (N/m) | | |
| Front waist zone | 27.4 | 36.3 |
| Front distal tummy zone | 27.4 | 29.8 |
| Front proximal tummy zone | 107.7 | 25.7 |
| Front leg zone | 19.5 | 22.1 |

TABLE 2-continued

|  | Example 1 | Comparative Example 1 |
|---|---|---|
| Back waist zone | 28.6 | 32.0 |
| Back distal tummy zone | 49.5 | 39.4 |
| Back proximal tummy zone | 32.5 | 20.4 |
| Back leg zone | 20.5 | 23.1 |

For Examples 1-2, the tensile stress of the front proximal tummy zone is highest among any other zone, and is more than 150% of the tensile stress of the back proximal zone. For Example 1, the tensile stress of the front proximal tummy zone is more than 200% of the tensile stress of the front distal tummy zone.

Also for Examples 1-2, the tensile stress of the front leg zone is no more than 60% of the tensile stress of the front proximal tummy zone, and the tensile stress of the back leg zone is no more than 100% of the tensile stress of the back proximal tummy zone.

For Comparative Example 1, the tensile stress of the front proximal tummy zone is lower than the tensile stress of the front distal tummy zone, and is less than 150% of the tensile stress of the back proximal zone. Also for Comparative Example 1, the tensile stress of the front leg zone is greater than the tensile stress of the front proximal tummy zone, and the tensile stress of the back leg zone is greater than the tensile stress of the back proximal tummy zone.

Example 1 provided profiling of tensile stress per zone without significant increase of total tensile force of the belt compared to Comparative Example 1.

Compared to Comparative Example 1, Examples 1-2 provide improvement in one or more of: fit, coverage of buttock area, comfort during wear, prevention of sagging, prevention of leakage, fit around waist, softness of inside of the belt, prevention of red marking, overall softness, looking soft, and perceived overall quality.

Consumer Acceptance

Example 1 and Comparative Example 1 including an identical absorbent core were subjected to a consumer test for application on 50 panelists and 51 panelists, respectively. The panelists were caregivers of Japanese Size 4 (L-size) wearers of age 0-36 months, and at about the same boy/girl ratio. The panelists were given enough products to use either product for 5 days, and then answer a questionnaire including the following questions, and asked to rate the performance in 5 scales from "Very Poor" to "Excellent", wherein 100 represents "Excellent", 75 represents "Good", 50 represent "Fair", 25 represent "Poor" and 0 represents "Very Poor". The ratings were averaged and statistically analyzed. Test results are shown below in Table 3.

TABLE 3

| Question | Example 1 | Comparative Example 1 |
|---|---|---|
| Overall Rating | 77* | 69 |
| Overall Softness | 86* | 71 |
| Belt Softness | 79 | 70 |
| Overall Fit Of The Pant When The Diaper Is Full | 72 | 64 |
| Overall Quality Of The Product | 80* | 71 |
| Preventing Skin Problems Such As Rash/Redness/Would Cause You Concern | 70 | 62 |
| Preventing Diaper Dropping & Sagging That Would Cause You Concern | 76 | 71 |

*Statistically significant over Comparative Example 1 with 90% confidence level

According to the consumer acceptance test results, Example 1 of the present invention, compared to Comparative Example 1, was accepted better in all aspects of the product listed above, and was statistically significantly better accepted in many aspects of the product. In particular, Example 1 was significantly conceived better in "Overall Rating", "Overall Softness", and "Overall quality of the product". This demonstrates that the article of the present invention is significantly better compared to an article of the prior art.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A wearable article continuous in a longitudinal direction and a transverse direction, comprising a main body and a ring-like elastic belt comprising a front belt and a back belt, the center of the front belt is joined to a front waist panel of the main body, the center of the back belt is joined to a back waist panel of the main body, the front and back belt each having a left side panel and a right side panel where the main body does not overlap, and the transverse edges of the front belt and the back belt are joined by a seam to form a waist opening and two leg openings, wherein each of the front belt and back belt are formed by an inner sheet, an outer sheet, and a plurality of elastic bodies sandwiched therebetween and running in the transverse direction substantially parallel to each other;

wherein each front belt and back belt have transversely continuous distal edges, each front belt and back belt having side edges;

wherein at least some of the elastic bodies disposed on either the front belt or the back belt are arranged in at least 2 sets of a concentrated array, the concentrated arrays meeting a), b), and c) as follows:

a) one concentrated array is formed by at least 2 elastic bodies;

b) each elastic body within the one concentrated array (of clause a) above) is disposed in an inner-interval in the longitudinal direction between each elastic body of 2-4 mm;

c) one specific concentrated array, outside of and separate from the one concentrated array, disposed in an extra-interval in the longitudinal direction between at least one neighboring elastic body outside the specific concentrated array of greater than the inner-interval of the specific concentrated array;

wherein the entirety of the length of the belt side edge of the front belt is seamed with a certain length of the belt side edge of the back belt to define a seam length LS;

the front and back belts each divided into 4 zones extending in the transverse direction and defined by its location from the distal edge to the percentage of the seam length LS wherein; 0-25% is the waist zone, 25-50% is the distal tummy zone, 50-85% is the proximal tummy zone, and 85-100% is the leg zone; and wherein at least one of the at least 2 concentrated arrays are disposed on the front proximal tummy zone.

2. The absorbent article of claim 1, wherein the elastic bodies of the one concentrated array have a density of no more than 940 dtex.

3. The absorbent article of claim 1, wherein the elastic bodies of the one concentrated array are disposed at an elongation of from 100% to 350%.

4. The absorbent article of claim 1, wherein the elastic belt comprises no more than 60 elastic bodies.

5. The absorbent article of claim 1, wherein the article has a Waist Circumference Force according to the Whole Article Force Measurement herein of no more than 10N.

6. The absorbent article of claim 1, wherein the tensile stress of the front proximal tummy zone is higher than the tensile stress of any other zone.

7. The absorbent article of claim 1, wherein the tensile stress of the back distal tummy zone is higher than the tensile stress of the front distal tummy zone.

8. The absorbent article of claim 1, wherein the tensile stress of the front leg zone is no more than 50% of the tensile stress of the front proximal tummy zone, and the tensile stress of the back leg zone is no more than 100% of the tensile stress of the back proximal tummy zone.

9. The absorbent article of claim 1, wherein the tensile stress of the front leg zone is no more than 40% of the tensile stress of the front proximal tummy zone.

10. The absorbent article of claim 1, wherein at least a portion of the elasticity of at least one of the elastic bodies is removed in the region overlapping with the front and back waist panels of the main body.

11. A wearable article continuous in a longitudinal direction and a transverse direction, comprising a main body and a ring-like elastic belt comprising a front belt and a back belt, the center of the front belt is joined to a front waist panel of the main body, the center of the back belt is joined to a back waist panel of the main body, the front and back belt each having a left side panel and a right side panel where the main body does not overlap, and the transverse edges of the front belt and the back belt are joined by a seam to form a waist opening and two leg openings, wherein each of the front belt and back belt are formed by an inner sheet, an outer sheet, and a plurality of elastic bodies sandwiched therebetween and running in the transverse direction substantially parallel to each other;

wherein each front belt and back belt have transversely continuous distal edges, each front belt and back belt having side edges;

wherein at least some of the elastic bodies disposed on either the front belt or the back belt are arranged in at least 2 sets of a concentrated array, the concentrated arrays meeting a), b), and c) as follows:

a) one concentrated array is formed by 2-4 elastic bodies;

b) each elastic body within the one concentrated array (of clause a) above) is disposed in an inner-interval in the longitudinal direction between each elastic body of 2-4 mm;

c) one specific concentrated array, outside of and separate from the one concentrated array, disposed in an extra-interval in the longitudinal direction between at least one neighboring elastic body outside the specific concentrated array of greater than the inner-interval of the specific concentrated array;

wherein the entirety of the length of the belt side edge of the front belt is seamed with a certain length of the belt side edge of the back belt to define a seam length LS;

the front and back belts each divided into 4 zones extending in the transverse direction and defined by its location from the distal edge to the percentage of the seam length LS wherein; 0-25% is the waist zone, 25-50% is the distal tummy zone, 50-85% is the proximal tummy zone, and 85-100% is the leg zone; and wherein at least one of the at least 2 concentrated arrays are disposed in the back distal tummy zone.

12. The absorbent article of claim 11, wherein the elastic bodies of the one concentrated array have a density of no more than 1100 dtex.

13. The absorbent article of claim 11, wherein the elastic bodies of the one concentrated array are disposed at an elongation of from 100% to 350%.

14. The absorbent article of claim 11, wherein the elastic belt comprises no more than 60 elastic bodies.

15. The absorbent article of claim 11, wherein the article has a Waist Circumference Force according to the Whole Article Force Measurement herein of no more than 10N.

16. The absorbent article of claim 11, wherein the tensile stress of the back distal tummy zone is higher than the tensile stress of the front distal tummy zone.

17. The absorbent article of claim 11, wherein the tensile stress of the front proximal tummy zone is higher than the tensile stress of any other zone.

18. The absorbent article of claim 11, wherein at least a portion of the elasticity of at least one of the elastic bodies is removed in the region overlapping with the front and back waist panels of the main body.

* * * * *